United States Patent [19]

Van der Veken et al.

[11] Patent Number: 4,672,126
[45] Date of Patent: Jun. 9, 1987

[54] PROCESS FOR ISOLATING LEVAMISOLE FROM TETRAMISOLE

[75] Inventors: Guido J. L. Van der Veken, Kasterlee; Eric J. Guns, Balen; Albert L. A. Willemsens, Beerse, all of Belgium

[73] Assignee: Janssen Pharmaceutica, N.V., Beerse, Belgium

[21] Appl. No.: 656,557

[22] Filed: Oct. 1, 1984

Related U.S. Application Data

[63] Continuation-in-part of Ser. No. 550,666, Nov. 10, 1983, abandoned.

[51] Int. Cl.[4] ............................................. C07D 513/02
[52] U.S. Cl. ..................................................... 548/155
[58] Field of Search ........................................ 548/155

[56] References Cited

U.S. PATENT DOCUMENTS 3,579,530  5/1971  Dewar et al. ...................... 548/155
3,580,923  5/1971  Leigh et al. ........................ 548/155

OTHER PUBLICATIONS

Bhatt et al. "Preparation and Antimicrobial Activity of L[+]α-Arylsulphonamido Succinic Acids and L[+]-Disodium-α-Aryl-sulphonamido Glutarates", Indian Chem. Journal, Sep. 1978, pp. 21–22.

*Primary Examiner*—Donald G. Daus
*Assistant Examiner*—Stephen M. Kapner
*Attorney, Agent, or Firm*—Geoffrey Dellenbaugh

[57] ABSTRACT

A process for isolating levamisole or a therapeutically acceptable acid addition salt thereof from tetramisole or an acid addition salt thereof by precipitating levamisole. L-N-[(4-methoxyphenyl)sulfonyl]-glutamic acid (salt) and converting the diastereomeric salt into levamisole or a suitable acid addition salt thereof.

9 Claims, No Drawings

PROCESS FOR ISOLATING LEVAMISOLE FROM TETRAMISOLE

CROSS REFERENCE TO RELATED APPLICATION

This application is a continuation in part of our co-pending application Ser. No. 550,666, filed Nov. 10, 1983, now abandoned.

DESCRIPTION OF THE INVENTION

Tetramisole, being chemically designated as 2,3,5,6-tetrahydro-6-phenylimidazo[2,1-b]thiazole, has been described in U.S. Pat. No. 3,274,209 and may chemically be represented by the formula

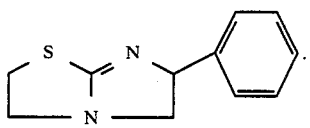

The anthelmintic activity of tetramisole is taught to be predominantly associated with its laevorotatory enantiomer, levamisole, which may be represented by the formula

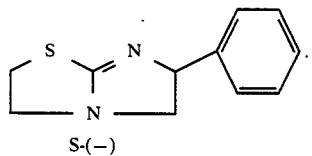

S-(−)

The dextrarotatory enantiomer, dextramisole, which may be represented by the formula

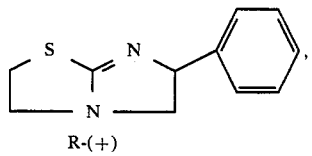

R-(+)

is taught to combine dramatically reduced anthelmintic activity with a toxicity for warm-blooded animals analogous to that of levamisole.

The combination of increased anthelmintic activity and a toxicity for warm-blooded animals analogous to the toxicity of the dextra-rotatory enantiomer results in an increased safety-margin in favour of levamisole, compared with the racemic tetramisole. Due to said increased safety-margin the use of the pure laevorotatory form has distinct advantages. Consequently several processes have been devised for the production of pure levamisole. Such processes are principally based either on the stereospecific preparations of levamisole starting from pure enantiomeric forms of suitable intermediates, or on the isolation of levamisole from a racemic mixture by a process called resolution.

Several processes for separating both enantiomers from tetramisole have been described. Said processes may generally be effected in three subsequent steps consisting of (i) mixing tetramisole with an appropriate optically active acid in a suitable solvent, thus forming a diastereomeric salt with one of the enantiomers;

(ii) collecting the precipitated diastereomeric salt; and (iii) isolating levamisole or an acid addition salt thereof from the diastereomeric salt or from the remaining liquid phase.

The above-mentioned process, generally known as fractional crystallization-process, has been described with several stereochemically isomeric forms of suitable acids such as, for example, with enantiomers of camphorsulfonic acid, enantiomers of tartaric acid or derivatives thereof and enantiomers of glutamic acid or derivatives thereof.

The applicability and, consequently, the choice of the fractional crystallization procedure and, more particularly, the choice of the resolving agent and the solvent used in the crystallization step depends upon several characteristics such as, for example, the yield of the diastereomeric salt, the purity of said salt, whether the (levamisole.resolving agent)-salt or the (dextramisole.-resolving agent)-salt crystallizes, the availability of the desired stereochemically isomeric form of the acid, the possibility to recover the resolving agent and the like.

Due to the availability of L-glutamic acid, said carboxylic acid and a number of derivatives thereof have frequently been described for the separation of racemic basic compounds into their enantiomers. Certain derivatives of L-glutamic acid have also been described as being useful resolving agents for the separation of tetramisole into levamisole and dextramisole, wherein a diastereomeric salt is precipitated from the reaction mixture. Suitable derivatives of L-glutamic acid are cited, for example, in U.S. Pat. No. 3,579,530, describing the use of a number of derivatives of the said acid wherein the amine function is substituted with a sulfonyl-group, such as, for example L-phenylsulfonylglutamic acids wherein the phenyl group is optionally substituted by nitro, bromo, fluoro or methyl.

It has now surprisingly been found that levamisole or a therapeutically acceptable acid addition salt thereof may be isolated from tetramisole or an acid-addition salt thereof in extremely high yields and desired purity by the consecutive steps of (i) mixing tetramisole or an acid addition salt thereof with a suitable amount of L-N-[(4-methoxyphenyl)sulfonyl]glutamic acid an alkali metal or earth alkaline metal salt thereof in a suitable solvent;

(ii) collecting the precipitated levamisole.L-N-[(4-methoxyphenyl)sulfonyl]glutamic acid (salt); and (iii) liberating levamisole from the said precipitated salt;

and optionally converting the thus obtained levamisole into a suitable acid addition salt.

The molar ratio of L-N-[(4-methoxyphenyl)sulfonyl]-glutamic acid to the amount of tetramisole is preferably at least 1:2, and since the resolving agent may be recovered in rather good yields a slight excess of L-N-[(4-methoxyphenyl)sulfonyl]glutamic acid, even up to 0.5 mole per mol of tetramisole, may be suitable. Although the subject process has the advantage that the yield of the precipitated levamisole.L-N-[(4-methoxyphenyl)-sulfonyl]glutamic acid salt is only neglectibly influenced by the excess-amount of L-N-[(4-methoxyphenyl)sulfonyl]glutamic acid used in the partial fractionation step, the molar ratio of L-N-[(4-methoxyphenyl)sulfonyl]glutamic acid to the amount of tetramisole is preferably comprised between 1:2 and 1:1.

Preferred salts of L-N-[(4-methoxyphenyl)sulfonyl]glutamic acid are the mono- and dialkali metal or earth alkaline metal salts thereof and, most preferably, the mono- and disodium or potassium salts thereof.

It is evident that the choice of tetramisole or suitable acid addition salts thereof as well as the choice of L-N-[(4-methoxyphenyl)sulfonyl]glutamic acid or a mono- or dialkali metal or earth alkaline metal salt thereof is determined by the nature of the solvent or the solvent mixture used in the crystallization step.

Conversely, the solvent or solvent mixture should be selected in such a way that tetramisole or the acid addition salt used as starting material as well as L-N-[(4-methoxyphenyl)sulfonyl]glutamic acid or the alkali- or earth alkaline metal salt thereof used as resolving agent are sufficiently soluble therein.

For example, when the solvent mixture is an aqueous or predominantly aqueous medium it is evident that both levamisole and L-N-[(4-methoxyphenyl)sulfonyl]glutamic acid are preferably used in salt form while the corresponding base and carboxylic acid forms are preferred where the crystallization-reaction is conducted in organic or predominantly organic medium.

Predominantly aqueous mediums as mentioned hereinabove are meant to include mediums containing at least 50% of water. Particularly preferred predominantly aqueous mediums are those containing not less than 80% of water.

Predominantly organic mediums as mentioned hereinabove are meant to include mediums containing not more than 50% of water. Particularly preferred predominantly organic mediums are those containing not more than 20% of water. The most preferred predominantly organic mediums are those containing from 3% to 10% of water.

It is evident that where acid addition salts of tetramisole and/or alkali metal or earth alkaline metal salts of L-N-[(4-methoxyphenyl)sulfonyl]glutamic acid are used as starting materials and resolving agents the crystallization of the diastereomeric salt may only be effected after adjustment of the pH of the mixture. Such adjustment may be accomplished, for example, by adding an appropriate amount of a suitable acid, e.g. hydrochloric acid and the like. The choice of the acid is only limited in that it may not form insoluble salts of dextramisole in the medium.

Furthermore, it can be stated that the yield and the purity of the isolated levamisole.L-N-[(4-methoxyphenyl)sulfonyl]glutamic acid (salt) is relatively independent from the solvent or the solvent mixture used in the fractional crystallization reaction-step, provided that the solubility of the diastereomeric salt is low in the said solvent or solvent mixture at relatively low temperature. Preferably, the solvent or solvent mixture is selected in such a way that the solubility of the diastereomeric salt is relatively high at elevated temperature while at decreased temperature said solubility is relatively low.

As levamisole has basic properties it may easily be liberated from the diastereomeric salt by treating the latter with an appropriate base, such as, for example, alkali metal or earth alkaline metal carbonates or hydroxides, e.g. sodium carbonate, potassium carbonate and the like, or organic bases such as, for example, pyridine, N,N-diethylethanamine and the like. A suitable method for liberating levamisole from the diastereomeric salt is, for example, by solubilizing the diastereomeric salt in a solvent-system consisting of a water-immiscible organic solvent and a suitable alkaline aqueous medium, e.g., aqueous sodium hydroxide, and extracting the aqueous phase with said water-immiscible organic solvent.

The L-N-[(4-methoxyphenyl)sulfonyl]glutamic acid present in the hereinabove mentioned aqueous phase may be recovered to be used in a subsequent resolution-cycle. Depending upon the particulars of the contemplated resolution process and the solvent used therein the L-N-[(4-methoxyphenyl)sulfonyl]glutamic acid may be used as such or after conversion into a suitable salt form. It is evident that the aqueous phase from the hereinabove-mentioned extraction procedure of L-N-[(4-methoxyphenyl)sulfonyl]glutamic acid in salt form may be used as such when the subsequent resolution-process is conducted in aqueous medium.

The levamisole, present in the hereinabove-mentioned water-immiscible organic solvent layer, may be isolated following art-known procedures.

Where levamisole is to be isolated in free base form it may be appropriate to crystallize the latter from the above-mentioned water-immiscible extract, if desired, after partial evaporation of the organic solvent or solvent mixture. Where levamisole is to be isolated in the form of a suitable therapeutically acceptable acid addition salt it may be appropriate to extract the levamisole from the water-immiscible medium with an aqueous solution of the desired acid and to crystallize the salt form from said solution, if desired, after partial evaporation of the aqueous medium. It is evident that the desired acid addition salts of levamisole may also be generated by adding a suitable amount of the desired acid to the water-immiscible extract. Since the above-mentioned isolation steps are concerned with crystallization-reactions it is evident that the yields as well as the rates of said reactions may be enhanced by decreasing the temperature of the crystallizing medium.

Levamisole, having basic properties, may be converted to its therapeutically acceptable acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzene sulfonic, cyclohexanesulfamic, 2-hydroxybenzoic, 4-amino-2-hydroxybenzoic and the like acids. Conversely each of the above-mentioned salt forms can be converted into the free base form by treatment with a suitable base.

The subject process for isolating levamisole from tetramisole combines a high yield of levamisole with a desired degree of purity. The process wherein L-N-[4-methoxyphenyl)sulfonyl]glutamic acid is used as resolving agent yields levamisole almost quantitatively and, at least, in yields higher than 90%.

When comparing the subject resolving process with prior art processes for resolving tetramisole in comparable circumstances, such as those described in U.S. Pat. No. 3,579,530, yields are considerably higher. Such superiority is completely unexpected, particularly since L-N-[(4-methoxyphenyl)sulfonyl]glutamic acid, which has been described in Indian Chemical Journal, 13, 21-22 (1978) as an agent having useful anti-microbial activity, has never been described as a resolving agent.

The diastereomeric salt of levamisole with L-N-[(4methoxyphenyl)sulfonyl]glutamic acid is new and, as a useful intermediate in the process according to the subject invention, this intermediate and a process for preparing it as described hereinabove constitute additional features of the present invention.

The following examples describing the yield of the resolution process, the optical rotation of the levamisole.L-N-[(4-methoxyphenyl)sulfonyl]glutamic acid (salt) obtained by this process, the possibility to recover the resolving agent and the yield and optical rotation of levamisole obtained from the levamisole.L-N-[(4-methoxyphenyl)sulfonyl]glutamic acid (salt) are intented to illustrate and not to limit the scope of the present invention.

EXPERIMENTAL PART

EXAMPLE I

To a warmed solution, 40° C., of 24.08 g of tetramisole hydrochloride (0.1 mol) in 113 ml. water adjusted to pH 4 with hydrochloric acid was added dropwise during a period of 50 minutes a suspension containing 15.85 g of L-N-[(4-methoxyphenyl)sulfonyl]glutamic acid (0.05 mol) and 2 g of sodium hydroxide (0.05 mol) in 85 ml of water. The mixture was cooled to 15°-20° C. and additionally stirred during 5 hours. The precipitate was filtered off, washed with water and dried under vacuo at 50° C., yielding 23.55 g of levamisole.L-N-[(4-methoxyphenyl)sulfonyl]glutamic acid (salt) (yield=90.3%); $\alpha_D^{20}=-63°$ ($c_5$, 1N HCl); mp. 127.4°-128.1° C.

EXAMPLE II

A mixture containing 82.5 g of L-N-[(4-methoxyphenyl)sulfonyl]glutamic acid (0.26 mol), 445 ml of water, 27.3 ml. sodium hydroxide 19.5 molar aqueous solution (0.53 mol) and 120.38 g of tetramisole hydrochloride (0.5 mol) was warmed up to 40° C. The warmed homogeneous mixture was adjusted to pH 4.2 with hydrochloric acid and cooled at 15° C. After 16 hours the precipitate was filtered off, washed and dried under vacuo at 50° C., yielding 127.44 g of levamisole.L-N-[(4-methoxyphenyl)sulfonyl]glutamic acid (salt) (yield=97.7%) $\alpha_D^{20}=-63.7°$ ($c_5$, 1N HCl); mp. 127.5°-128.3° C.

EXAMPLE III

A mixture containing 11.39 kg of L-N-[(4-methoxyphenyl)sulfonyl]glutamic acid (35.9 mol), 61 l of water, 3.77 l sodium hydroxide 19.5 molar aqueous solution (73.5 mol) and 16.61 kg of tetramisole hydrochloride (69 mol) was warmed up to 40° C. The homogeneous mixture was adjusted to pH 4.2 with hydrochloric acid and cooled at 15° C. After 18 hours the precipitate was filtered off, washed and dried under vacuo at 50° C., yielding 17.15 kg of levamisole.L-N-[(4-methoxyphenyl)sulfonyl]glutamic acid (salt) (yield: 95%); $\alpha_D^{20}=65.1°$ ($c_5$, 1N HCl); mp. 127.9°-129.4° C.

EXAMPLE IV

To a refluxing solution of 20.43 g of tetramisole (0.1 mol) in 190 ml of 2-propanone and 10 ml. of water was added 15.9 g of L-N-[(4-methoxyphenyl)sulfonyl]glutamic acid (0.05 mol). The mixture was refluxed for another 5 minutes and cooled to 15° C. After 12 hours the precipitate was filtered off, washed with 2-propanone and dried under vacuo at 70° C., yielding 23.88 g of levamisole.L-N-[(4-methoxyphenyl)sulfonyl]glutamic acid (salt) (yield=91.6%) $\alpha_D^{20}=-63.5°$ ($c_5$, 1N HCl); mp. 127.6°-129.3° C.

EXAMPLE V

Following the procedure described in Example IV the following fractional crystallization reactions have also been effected:

| amount of solvent or solvent mixture in ml | amount of tetramisole.base in moles | Yield in % | $\alpha_D^{20}$ ($c_5$,1N HCl) | mp. °C. |
|---|---|---|---|---|
| (1) 2-propanol + water<br>142.5 ml    7.5 ml | 0.1 | 95.6 | −63.1° | 127.1-128.7 |
| (2) tetrahydrofuran + water<br>142.5 ml    7.5 ml | 0.1 | 93.8 | −62.8° | 127.3-129.0 |
| (3) methylbenzene + 2-propanone + water<br>60 ml    115 ml    6.75 ml | 0.1 | 94.6 | −63.1° | 127.1-128.7 |
| (4) 2-propanone<br>400 ml | 0.1 | 90.8 | −59.2° | 127.0-128.5 |

EXAMPLE VI

A solution of 15.65 kg of levamisole.L-N-[(4-methoxyphenyl)sulfonyl]glutamic acid (salt) (30.02 mol) dissolved in 20.3 l water and 3,15 l sodium hydroxide 19.5 molar aqueous solution was extracted with 30.4 l of methylbenzene at 40° C. and the aqueous layer was washed with 7.5 l methylbenzene. Weighing of the combined water layers and determination of the concentration of the di-sodium salt of L-N-[(4-methoxyphenyl)sulfonyl]glutamic acid yields a 97% amount of di-sodium salt of L-N-[(4-methoxyphenyl)sulfonyl]glutamic acid. To the combined water layers were added 25.2 l water and 13.48 kg of tetramisole hydrochloride. After warming up at about 45° C. the aqueous solution was adjusted to pH 4.2 with hydrochloric acid and cooled at 15° C. After 18 hours the precipitate was filtered off, washed and dried under vacuo at 50° C. yielding 14.27 kg of levamisole.L-N-[(4-methoxyphenyl)sulfonyl]glutamic acid (salt) (yield: 97.7%); $\alpha_D^{20}=-64.1$ ($c_5$. 1N HCl); mp. 127.8°-129.3° C..

EXAMPLE VII

A suspension of 31.73 g of L-N-[(4-methoxyphenyl)sulfonyl]-glutamic acid (0.1 mol) in 400 ml of water was stirred and heated till all solid entered solution. Then there were added 20.43 g of tetramisole (0.1 mol) and stirring while heating was continued for a while. The thus obtained homogeneous solution was further stirred for 4 hours while the temperature was allowed to reach room temperature. The precipitate was filtered off, washed with water and dried under vacuo at 50° C., yielding 25.58 g levamisole.L-N-[(4-methoxyphenyl)-sulfonyl]glutamic acid (salt) (yield 98.1%) $\alpha_D^{20} = -64.2°$ (c$_5$. 1N HCl); mp. 127.9°–129.4° C.

EXAMPLE VIII

A suspension of 31.73 g of L-N-[(4-methoxyphenyl)-sulfonyl-glutamic acid (0.1 mol) in 400 ml of 2-propanone and 20 ml of water was stirred and heated till all solid entered solution. Then there were added 20.43 g of tetramisole. The whole was stirred and heated to reflux and additionally stirred at reflux for 10 minutes. The mixture was further stirred for 4 hours while the temperature was allowed to reach room temperature. The precipitate was filtered off, washed with 100 ml of 2-propanone and 5 ml of water and dried under vacuo at 50° C., yielding 25.55 g of levamisole.L-N-[(4-methoxyphenyl)sulfonyl]glutamic acid (salt) (yield 98%) $\alpha_D^{20} = -62.4°$ (c$_5$. 1N HCl); mp. 127.3°–129° C.

EXAMPLE IX

A suspension of 31.73 g of L-N-[(4-methoxyphenyl)-sulfonyl]-glutamic acid (0.1 mol) in 400 ml of 2-propanol and 20 ml of water was stirred and heated till all solid entered solution. Then there were added 20.43 g of tetramisole. The whole was stirred and heated till an homogeneous solution was obtained. The solution was further stirred for 4 hours while the temperature was allowed to reach room temperature. The precipitate was filtered off, washed with 100 ml of 2-propanol and 5 ml of water and dried under vacuo at 50° C., yielding 26.17 g levamisole.L-N-[(4-methoxyphenyl)-sulfonyl]glutamic acid (salt) (yield 100.3%) $\alpha_D^{20} = -62.8°$ (c$_5$. 1N HCl); mp. 127.4°–129.1° C.

EXAMPLE X

A suspension of 7.82 kg of levamisole.L-N-[(4-methoxyphenyl)sulfonyl]glutamic acid (salt) (15 mol) in 10.1 l of water and 15.2 l of methylbenzene was alkalized with 1.6 l of 50% sodium hydroxide aqueous solution and warmed to 40° C. The organic layer was separated, the aqueous layer washed with 3.75 l of methylbenzene and the combined organic layers were dried. 51 g of norit were added and after 20 minutes stirring at room temperature the suspension was filtered over a diatomaceous earth and washed with 1.9 l of methylbenzene. The filtrate was acidified with 2-propanol/HCl to ph$\leq$1, cooled slowly to 20° C. and cooled further to 0° C. during 18 hours. The precipitate was filtered off, washed with 2-propanol, and dried under vacuo at 80° C., yielding 34 kg of levamisole hydrochloride (yield 94.2%); $\alpha_D^{20} = -127°$ (c$_5$. H$_2$O); mp. 229.5° C.

What is claimed is:

1. A process for isolating levamisole or a therapeutically acceptable acid addition salt thereof from tetramisole or an acid addition salt thereof by the consecutive steps of:
   (i) mixing tetramisole or an acid addition salt thereof with a suitable amount of L-N-[(4-methoxyphenyl)sulfonyl]glutamic acid or an alkali metal or earth alkaline metal salt thereof in a suitable solvent;
   (ii) collecting the precipitated levamisole.L-N-[(4-methoxyphenyl)sulfonyl]glutamic acid (salt); and
   (iii) isolating levamisole from the said precipitated salt;
   and optionally converting levamisole into a suitable therapeutically acceptable acid addition salt.

2. A process according to claim 1 wherein the molar ratio of the amount of L-N-[(4-methoxyphenyl)sulfonyl]glutamic acid to the amount of tetramisole is from 1:2 to 1:1.

3. A process for isolating levamisole or a therapeutically acceptable acid addition salt thereof from tetramisole by the consecutive steps of:
   (i) mixing L-N-[(4-methoxyphenyl)sulfonyl]glutamic acid with tetramisole in a molar ratio from 1:2 to 1:1 in a predominantly organic medium;
   (ii) collecting the precipitated levamisole.L-N-[(4-methoxyphenyl)sulfonyl]glutamic acid (salt); and
   (iii) isolating levamisole from the said precipitated salt;
   and optionally converting levamisole into a suitable therapeutically acceptable acid additional salt.

4. A process according to claim 3 wherein the predominantly organic medium contains not more than 20% of water.

5. A process according to claim 3 wherein the predominantly organic medium contains from 3% to 10% of water.

6. A process for isolating levamisole or a therapeutically acceptable acid addition salt thereof from a tetramisole acid addition salt by the consecutive steps of:
   (i) mixing a suitable alkali metal or earth alkaline metal salt of L-N-[(4-methoxy-phenyl)sulfonyl]glutamic acid with a suitable acid addition salt of tetramisole in a molar ratio from 1:2 to 1:1 in a predominantly aqueous medium;
   (ii) collecting the precipitated levamisole.L-N-[(4-methoxyphenyl)sulfonyl]glutamic acid (salt); and
   (iii) isolating levamisole from the said precipitated salt;
   and optionally converting levamisole into a suitable therapeutically acceptable acid addition salt.

7. A process according to claim 6 wherein the predominantly aqueous medium contains at least 80% of water.

8. Levamisole.L-N-[(4-methoxyphenyl)sulfonyl]glutamic acid (salt).

9. A process for preparing levamisole.L-N-[(4-methoxyphenyl)sulfonyl]glutamic acid (salt) from tetramisole or an acid addition salt thereof by mixing tetramisole or an acid addition salt thereof with a suitable amount of L-N-[(4-methoxyphenyl)sulfonyl]glutamic acid

* * * * *

UNITED STATES PATENT AND TRADEMARK OFFICE
CERTIFICATE OF CORRECTION

PATENT NO. : 4,672,126
DATED : June 9, 1987
INVENTOR(S) : Guido J. L. VanDer Veken It is certified that error appears in the above-identified patent and that said Letters Patent is hereby corrected as shown below:

Column 8, line 58, after "acid" insert --or an alkali metal or earth metal salt thereof in a suitable solvent and collecting the precipitated salt.--

Signed and Sealed this

Seventeenth Day of January, 1989

Attest:

DONALD J. QUIGG

*Attesting Officer*  *Commissioner of Patents and Trademarks*